United States Patent [19]

Vaillancourt

[11] 4,276,170
[45] * Jun. 30, 1981

[54] VENTED FLEXIBLE FILTRATION DEVICE FOR USE IN ADMINISTERING PARENTERAL LIQUIDS

[75] Inventor: Vincent L. Vaillancourt, Livingston, N.J.

[73] Assignee: Critikon, Inc., Tampa, Fla.

[*] Notice: The portion of the term of this patent subsequent to Jan. 3, 1995, has been disclaimed.

[21] Appl. No.: 23,873

[22] Filed: Mar. 26, 1979

Related U.S. Application Data

[63] Continuation-in-part of Ser. No. 934,107, Aug. 16, 1978, abandoned, which is a continuation of Ser. No. 814,372, Jul. 8, 1977, abandoned, which is a continuation-in-part of Ser. No. 736,670, Oct. 28, 1976, Pat. No. 4,066,556.

[51] Int. Cl.³ .............................................. B01D 19/00
[52] U.S. Cl. ..................................... 210/436; 55/156; 210/448; 210/472; 210/484
[58] Field of Search ............. 128/214 R; 55/159, 185, 55/522, 524, 307, 321–324, 158; 210/433 R, 433 M, 120, 472, 500 M, 436, 446, DIG. 23, 448, 483, 484

[56] References Cited

U.S. PATENT DOCUMENTS

| 3,523,408 | 8/1970 | Rosenberg | 55/156 |
| 3,631,654 | 1/1972 | Riely et al. | 55/324 |
| 4,035,304 | 6/1975 | Watanabe | 210/446 |

*Primary Examiner*—Frank Sever
*Attorney, Agent, or Firm*—Donald B. Tobin

[57] ABSTRACT

A vented filtration device comprising a closed, flexible and compressible housing having a liquid inlet and a liquid outlet. The housing includes an internal passage connecting the inlet and the outlet. A liquid filter assembly is disposed within the passage between the inlet and outlet thereby defining an upstream pressure section between the inlet and the filter and a downstream pressure section between the filter and the outlet. This assembly includes a flexible, porous bacteria retentive filter membrane, a flexible, porous support material overlying one surface of the filter membrane and a frame having at least one large central opening overlying the opposite surface of the filter membrane. A gas vent located in the housing communicating with the upstream pressure section of the passage is adapted to allow gas but not liquid to pass from the upstream section out of the housing.

10 Claims, 11 Drawing Figures

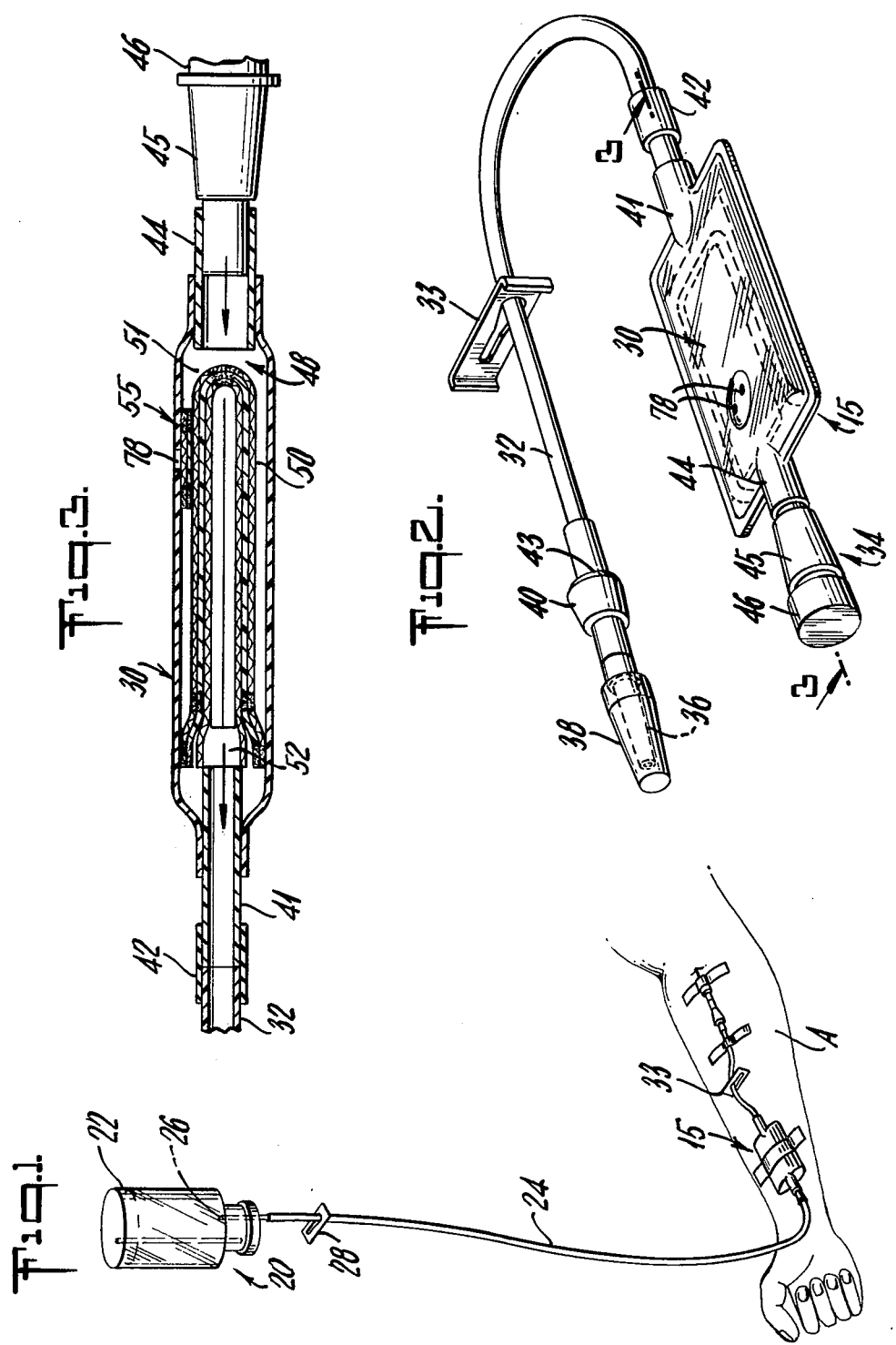

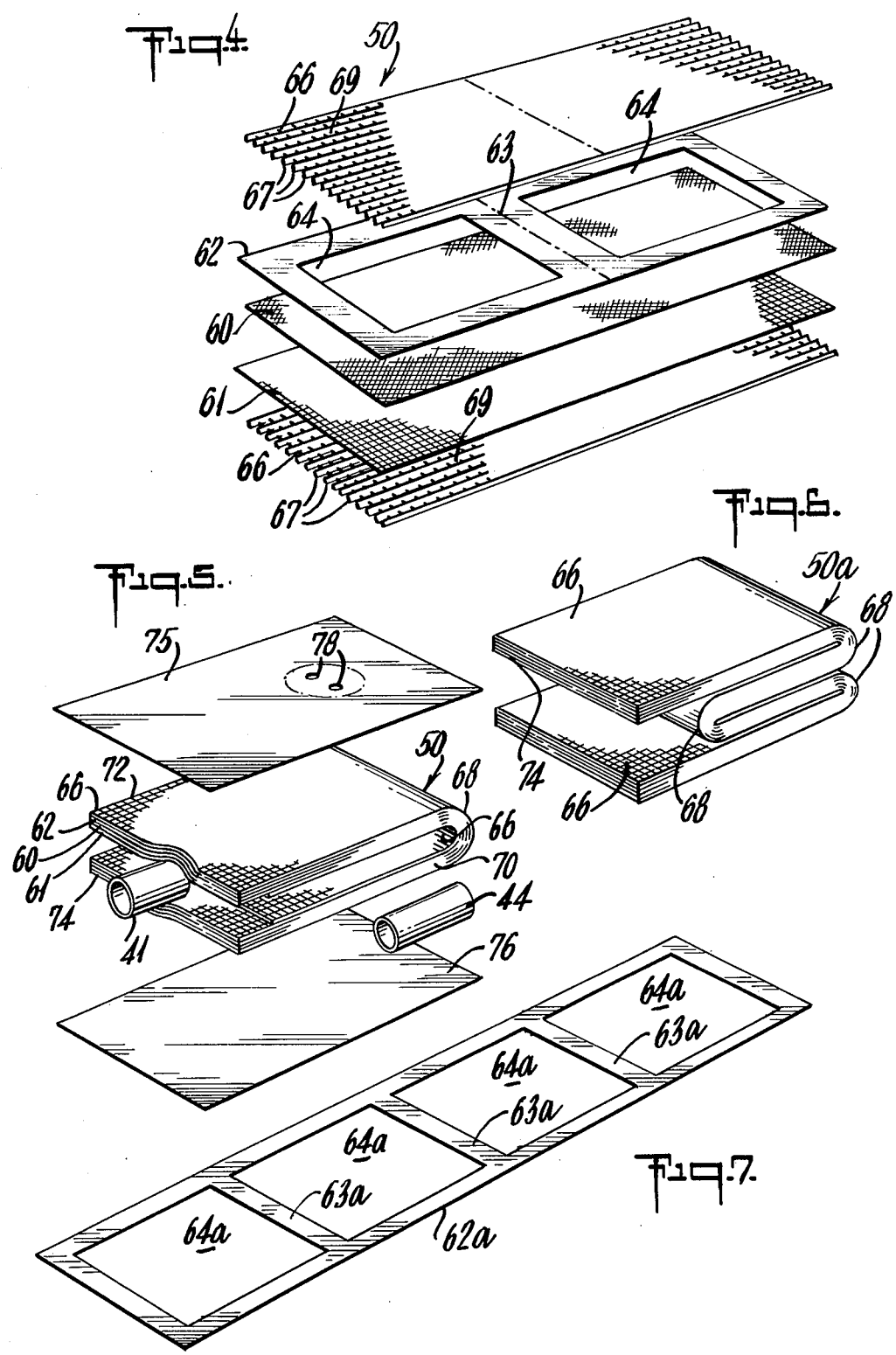

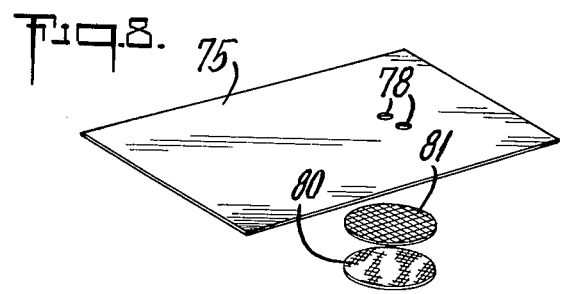
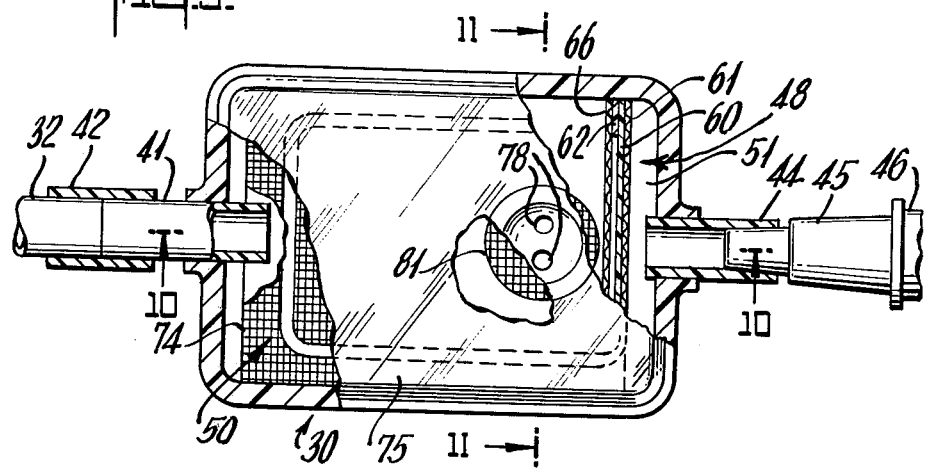
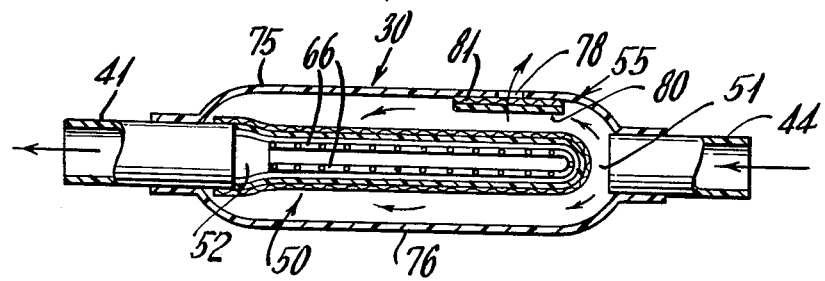
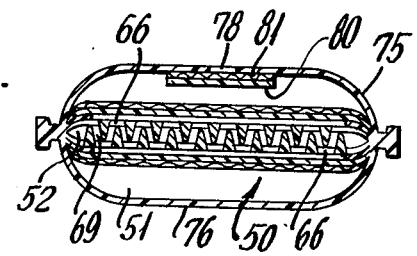

VENTED FLEXIBLE FILTRATION DEVICE FOR USE IN ADMINISTERING PARENTERAL LIQUIDS

This application is a continuation-in-part of application Ser. No. 934,107, filed Aug. 16, 1978 now abandoned, which is a continuation of application Ser. No. 814,372, filed July 8, 1977, now abandoned, which is a continuation-in-part of application Ser. No. 736,670, filed Oct. 28, 1976, now issued as U.S. Pat. No. 4,066,556.

BACKGROUND OF THE INVENTION

The present invention relates to a liquid filter assembly and, more particularly, to unique vented filter assemblies which purge air therefrom in the filtering of parenteral and other liquids during the administration thereof.

For some time it has been the preferred practice to filter intravenous and other parenteral solutions prior to the administration of such solutions to a patient to remove particulate matter that may be present in the solutions. Many different filter structures have been utilized for this purpose and many different procedures have been devised to insure that the liquids are properly filtered and administered with the highest degree of safety for the patient.

Recently, filter media have become commercially available that permit the filtration of intravenous liquids down to a particle size of about 0.22 microns. This is significant in that a filter having this pore size effectively serves as a bacteria retentive screen and filters out all bacteria from the liquids in addition to removing particulate matter. Heretofore, one of the main drawbacks of utilizing a 0.22 micron filter was that a very high pressure drop was created by the presence of the filter, thus, necessitating the use of a pump to sufficiently overcome the back pressure. Also, the 0.22 micron membrane filter media that have been found to be particularly applicable for use in the filtering of intravenous liquids are exceptionally difficult to handle during the fabrication of the filter media into appropriate filter structures. This is true because most of such filter media have very low tear strengths and do not form adequate heat seals with other plastic materials. Therefore, the geometrical configurations heretofore available with the 0.22 micron membrane filter media have been relatively flat surfaces which greatly limit, because of size considerations, the available filter area for the passage of liquids. Thus, the problem of excessive back pressure is increased because of the relatively small filtering surfaces.

Another significant problem encountered in the use of prior filters was that of air blockage due to improper priming. Since the type of liquid filters contemplated by this invention have hydrophilic properties, they do not pass air and, consequently, air accumulates at the filter surface and reduces the available filtration area. The result of this air accumulation at the filter surface is that it reduces the flow rate and contributes to the malfunction of the system. A significant portion of this problem may be overcome by priming the filter assembly prior to its use; however, since prior filters have been constructed from relatively rigid housing materials, this priming technique has been relatively complicated and has not always been effective in removing all of the air from the filter housing.

One of the ways to prime the filter has been to separate the filter assembly itself from the intravenous tubing so that air can escape from the filter. This, of course, requires the attendant to not only observe the intravenous flow for air blockage of the filter, but also to interrupt the intravenous feeding procedure to purge the air which is causing a blockage. As air enters the intravenous line due to a number of causes, it becomes necessary to constantly monitor the flow since the air does not purge itself, but requires some action on the part of the attendant or clinician.

A filter adapted to separate gases and liquids while performing the filtration function is disclosed in U.S. Pat. No. 3,854,907. A non-wetting filter material allows gases inside the filter cover to be vented through a relatively long tubular cylinder and to be conducted to an outlet port in the bottom of the filter cover. This structure represents one way in which undesirable gas or air entering into a fluid filter assembly with fluid may be removed. Thus, there is room for further improvements in simplicity of structure, cost of manufacture, convenience of use and handling, and in performance and specific functions of a vented filter assembly.

SUMMARY OF THE INVENTION

A vented filtration device comprises a closed, flexible and compressible housing having a liquid inlet and a liquid outlet. Included in the housing is an internal passage connecting the inlet and the outlet. A liquid filter assembly is disposed within the passage between the inlet and the outlet thereby defining an upstream pressure section between the inlet and the filter and a downstream pressure section between the filter and the outlet. The filter assembly includes a flexible, porous bacteria retentive filter membrane and a flexible, porous support material, having pores generally greater in size than those of the filter membrane, overlying one surface of the filter membrane. A flexible frame overlies the opposite surface of the filter membrane and has at least one central opening exposing a substantial surface area of the filter membrane. This filter assembly is adapted to filter all liquid passing from the inlet to the outlet during use. Gas vent means through the housing communicating with the upstream pressure section of said passage is adapted to allow gas but not liquid to pass from the upstream section out of the housing.

In the preferred embodiment the vented filtration device is comprised of a pair of flexible plastic sheets to form the housing, and the filter assembly is folded to form a flexible pouch having a liquid opening in one end thereof with the outlet communicating with the interior of the filter pouch through the filter opening. Included in the pouch is means to prevent the collapse of the flexible pouch on itself and thereby allow the flow of liquid therethrough when liquid passes from the passage through the pouch and into the interior thereof. In this embodiment, the gas vent includes at least one opening in the housing wall and a hydrophobic filter medium attached to the housing wall to cover the opening thereby allowing undesirable air inadvertently entering the housing with liquid to pass out of the housing through the vent.

Also in the preferred embodiment of this invention, the liquid filter membrane is formed from a porous non-woven nylon substrate coated with a copolymer of acrylonitrile and polyvinylchloride. This membrane of this material has hydrophilic properties. From the structural standpoint, the vented filtration device of the present invention is notably different from prior filter assemblies, for example, the filter holder disclosed in U.S. Pat. No. 3,854,907. Specifically, the present vented filtration device is more simple in construction and includes the gas vent directly in the housing wall rather than through an elongated passage as taught in the aforementioned patent. Furthermore, the flexible housing, the flexible liquid filter pouch and the means for preventing collapse of that pouch during liquid flow in the preferred embodiment of the present invention are features which individually and collectively contribute to the uniqueness of the present vented filtration device. In accordance with the principles of this invention, the vented filtration device overcomes the problem of air blockage of the liquid filter during administration of intravenous and other fluids. In the present vented filtration device, gas, such as air in the intravenous fluid is purged, automatically, or on its own, without the need for any priming. This advantageous feature obviates the necessity for close monitoring of the intravenous system for air blockage, and moreover, eliminates the need, as in many previously known systems, to break and interrupt the intravenous flow to prime the filter and purge the air.

Another advantage of the present invention, particularly in the preferred embodiment hereof, is the ability to allow air to escape from the filter assembly irrespective of its orientation during fluid administrations; i.e., the vented filter assembly does not have to be maintained in an upright or sideward position to take advantage of gravitational forces, since the construction of the preferred embodiment allows the escape of air and passage of liquid therethrough independent of gravitational orientation.

It has been found that usage of a thin, flexible porous bacteria retentive filter membrane, such as polycarbonate film, in a flexible housing, such as the present invention proposes, can be problematical. Since the housing of the present invention can be squeezed, compressed, twisted and bent during handling and use, the filter membrane has to be able to survive this abuse, whether inadvertent or not, and still be able to function as a bacteria filter medium. However, polycarbonate film and the like, as alluded to above, is very fragile and tends to crack, break and tear under certain stress conditions that may be encountered during handling and use. Accordingly, the present invention provides compensating factors to overcome this problem of fragility. The frame is used to support one surface of the filter membrane and to provide the medium for sealing the edges of the folded pouch together and to seal the pouch to the flexible housing during fabrication of the device. On the other surface of the filter membrane is a support material which serves as a buffer to absorb the stress which the filter membrane may encounter during use. Both the frame and the support material thus assist in making the fragile bacteria retentive filter membrane a functional reality in a flexible filtration device.

Of course, the advantage of a filtration device with a flexible housing is most desirable since it can be placed conveniently and comfortably on an arm of a patient during use. At present, all filters embodying a bacteria retentive filter have rigid housings, such as acrylic plastic. These devices are not only uncomfortable if placed on the arm of a patient during parenteral liquid administration, but are susceptible to breakage, especially if the patient should roll over or cause the device to be knocked or abused. Therefore, since it has not been feasible, on a commercial basis, to provide a flexible filtration device which filters bacteria from parenteral solutions during administration to a patient, the present invention serves as a unique and highly desirable improvement since it solves those problems as outlined above and satisfies the demands of the ultimate users of such devices.

BRIEF DESCRIPTION OF THE DRAWINGS

FIG. 1 is a perspective view illustrating a unique vented filtration device of the present invention in place during the administration of intravenous liquids into a patient;

FIG. 2 is a perspective view illustrating the entire filtration device of one embodiment of the present invention;

FIG. 3 is an enlarged cross-sectional view taken along line 3—3 of FIG. 2;

FIG. 4 is an exploded perspective view of the elements of one filter assembly pouch of the present invention;

FIG. 5 is a perspective view illustrating the fabrication of the filtration device;

FIG. 6 is a perspective view illustrating an alternate folding configuration of the filter assembly pouch;

FIG. 7 is a perspective view illustrating a frame for use in the alternate filter assembly pouch of FIG. 6;

FIG. 8 is a perspective view illustrating the elements of one gas vent of the filtration device;

FIG. 9 is an enlarged plan view of one embodiment of the filtration device with portions broken away to illustrate internal structure and liquid flow therethrough;

FIG. 10 is a cross-sectional view taken along line 10—10 of FIG. 9; and

FIG. 11 is a cross-sectional view taken along line 11—11 of FIG. 9.

DETAILED DESCRIPTION

While this invention is satisfied by embodiments in many different forms there is shown in the drawings and will herein be described in detail preferred embodiments of the invention, with the understanding that the present disclosure is to be considered as exemplary of the principles of the invention and is not intended to limit the invention to the embodiment or embodiments illustrated. The scope of the invention will be pointed out in the appended claims.

Adverting to the drawings, particularly to FIG. 1, one embodiment of the vented filtration device of the present invention is illustrated generally at numeral 15 attached to the arm A of a patient during the administration set shown generally at 20. Administration set 20 comprises an intervenous or parenteral solution container 22 which may be in the form of a glass bottle, plastic bag or other suitable means, and is preferably suspended approximately 2 to 3 feet (0.71 to 0.92 m.) above the administration cite. A length of tubing 24 having a spike 26 at the upper end thereof for penetrating the closure of intravenous solution container 22 extends downwardly from the container and delivers the intravenous liquid to filter assembly 15. A clamp 28 may be provided in tubing 24 to control the flow of liquid therethrough. Also, appropriate flow control devices, such as drip chambers or other liquid control apparatus, may be associated with tubing 24, if desirable. This equipment is well known in the art of administering intravenous solutions and will not be described in further detail herein.

Referring to FIG. 2, vented filtration device 15 is illustrated in greater detail and is shown to have a closed, flexible, compressible housing 30, a length of extension tubing 32 extending from one end of housing 30 and a connector 34 attached to the other end of housing 30. Tubing 32 is adapted to be connected to a conventional intravenous catheter assembly and to deliver filtered parenteral liquid from the downstream (distal) end of housing 30 to the intravenous catheter and, thus, into a vein of the patient. A suitable clamp 33 may be provided to control the flow of liquid through tubing 32. A connector 36 is attached to the end of tubing 32 and is equipped with a male fitting that is adapted to be received into a female fitting on an intravenous catheter. A cap 38 is positioned over connector 36 to protect and preserve the sterility of the connector. Of course, cap 38 must be removed from connector 36 prior to the attachment of the connector to the intravenous catheter. Connector 36 is attached in fluid communication to the end of tubing 32 by a fitting 40 which is preferably made of natural rubber, or a similar elastomer, which may be utilized as an injection site for medicaments or other liquids into the system. This injection is preferably accomplished by inserting the needle of a syringe or other device into the tapered angular shoulder 43 provided on the fitting.

In FIG. 3, the contents of the vented filtration device are illustrated. A liquid outlet formed by a relatively short length of tubing 41 is provided in the downstream, distal end of housing 30 and tubing 32 is connected to tubing 41 by a sleeve 42 positioned over the mating ends of each of the pieces of tubing. A heat seal or other appropriate attachment means may be utilized to facilitate bonding of these three elements together. The upstream, or proximal, end of housing 30 is also provided with a relatively short length of tubing 44 which provides a liquid inlet into housing 30 for the intravenous or parenteral solution supplied by container 22. A female fitting 45 is secured in the proximal end of tubing 44 and is adapted to be connected to a male fitting on the distal end of tubing 24. A cap 46 is positioned in the proximal end of fitting 45 to preserve the cleanliness of the system and to protect the fitting. Of course, cap 46 must be removed from fitting 45 prior to the connection of tubing 24 thereto. Inside housing 30 is a passage 48 connecting the inlet and outlet formed by the short tubing pieces. Disposed in passage 48 is a flexible filter assembly pouch 50 with a liquid opening in one end thereof. This liquid opening surrounds a portion of outlet tubing 41 so that the outlet communicates with the interior of filter assembly pouch 50 through the liquid opening therein. The disposition of pouch 50 thereby defines an upstream pressure section 51 in the passage between inlet tubing 44 and filter pouch 50, and a downstream pressure section 52 in the passage between pouch 50 and the outlet tubing 41. In the filtration device of the present invention, some positive pressure is required across the filter assembly pouch to force fluid through it; this positive pressure is on the upstream pressure section of the passage in the filter assembly. A gas vent 55 is located in one wall of housing 30 and communicates with upstream section 51 of the passage. Gas vent 55 is adapted to allow gas but not liquid to pass from upstream section 51 of the passage out of housing 30, and will be discussed hereinafter in greater detail.

Turning to FIG. 4, the elements of the preferred filter assembly pouch of the present invention are illustrated in detail. A hydrophilic membrane bacteria retentive filter sheet or film 60 is illustrated positioned adjacent a sheet of flexible, porous support material 61. Because filter sheet 60 generally possesses a relatively low flex strength in this application of the sheet, it has been found to be desirable to provide a reinforcing, or support, layer over substantially the entire outer surface area of the film to prevent rupture, or other failure, of the film during use. Support layer 61 selected for this embodiment preferably is a strip of nylon material, approximately 0.006 in. (0.015 cm.) thick, with pore sizes generally greater than 20 microns. This support material is formed with preferably rectangular dimensions to support filter sheet 60. This support material has been found to provide effective support for hydrophilic filter sheet 60 without substantially affecting the flow rate of the fluid. Other support layer materials may also be employed, such as non-apertured non-woven fabric composed of cellulosic wood pulp and polyester fibers bonded overall with a resin adhesive.

It will be seen in FIG. 4 that hydrophilic filter sheet 60 and support sheet 61 have a flexible frame member 62 disposed over the opposite surface of the filter sheet. Frame 62 preferably has a central support member 63 to add reinforcement when folded over. The use of flexible frame 62 has been found to be beneficial when it is desirable to test the efficacy of the seal and burst strength of filter sheet 60 prior to the incorporation of filter assembly pouch 50 into a filter assembly, while it also contributes to the formation of the heat seals during the fabrication of the filtration device. It is noted that frame 62 has generally large rectangular openings 64 to allow liquid to flow through hydrophilic filter sheet 60 in an unobstructed fashion. It has been found that a frame of thin, thermoplastic material is most compatible for incorporation in pouch 50 of this invention.

Positioned above frame 62 and below support material 61, respectively is a flat, porous scrim material 66 with a plurality of ridges 67 defining a plurality of channels 69 on one surface. Ridges 67 are spaced from each other so that channels 69, running substantially parallel to each other along the long dimension of the scrim material are provided. The preferable material for the scrim material is a ridged polyvinylchloride scrim wherein the ridges are the longitudinally running filaments which form the scrim. It can be appreciated that the scrim material may take many different forms, and may even be a sheet of porous material such as a knitted polyester net; the purpose of the scrim is to prevent the walls of the folded pouch from collapsing on each other, thereby preventing liquid flow, while allowing liquid to flow into, then out of, the pouch. It is appreciated that the scrim material is positioned on the innermost and outermost layers of the pouch assembly especially when the pouch has more than one fold, thus serving as a preventative measure for preventing collapse of the pouch on itself during use. It is also appreciated that, when collapse of the pouch on itself is not a problem, the scrim materials need not be incorporated in the assembly, or only one need be used if only one fold of the pouch is employed.

While many embodiments of the filter assembly pouch of this invention may be fabricated without support sheets or frame members, the filter media contemplated for use with the present invention are membrane-type materials that have the capability of filtering particles and bacteria having a size down to 0.22 microns; these are known as "bacteria retentive" filters and are sufficiently functional to prevent even the smallest bacteria such as pseudomonas diminutae from passing therethrough. The presently available commercial material usable in this type of application must be handled with care during fabrication. For example, it has been found that most available membrane filter media of this type have a common problem with regard to sealing, that is, the filter media do not lend themselves to conventional sealing techniques, such as heat sealing, solvent sealing, ultrasonic sealing, etc. To overcome these drawbacks, one aspect of the present invention is to provide a unique procedure for support and/or reinforcing this type membrane filter medium and for fabricating it in a pouch configuration into the filter housing. The fabrication of the filter assembly with filter assembly pouch 50 included therein is more clearly seen in FIG. 5. Filter pouch 50 containing hydrophilic filter sheet 60 has been formed in this embodiment utilizing support sheet 61, frame member 62 and two scrim materials 66, one on each outside surface of the layered configuration. This multi-layered stack or combination has been folded substantially in half along a fold line 68 to form filter assembly pouch 50 having folded edge 68, two edges 70 and 72 adjacent the folded edge and an open edge 74 opposite folded edge 68. This folded pouch is folded so that one scrim material 66 will be completely disposed within the completed pouch 50 upon final assembly, while the other scrim material 66 is on the outside surface. Inserted in edge 74 between the folded layers is outlet tubing 41; tubing 41 communicates with the interior of folded pouch 50, and protrudes outwardly for use as a liquid outlet in the completed filtration device.

If increased filtration area is desirable for certain applications of the present filtration device it is possible to fold the filter assembly more than one time when forming the flexible pouch. For instance, in FIG. 6, filter assembly 50a has been folded three times at fold lines 68 to form an "M" like appearance. Note that in this configuration both innermost and outermost scrim materials 66 are functional to prevent collapse of the pouch on itself during use since an extra leg of the pouch has been added. While three folds are employed in this embodiment, the edges along the sides are sealed as in the previously described embodiment, and the open end 74 is utilized to include the appropriate tubing for communicating with the inlet or outlet, whichever is preferred. When folding the filter assembly three times as illustrated in FIG. 6, it is preferable to use a frame with a plurality of centrally located openings such as shown in FIG. 7. Frame 62a has four central openings 64a, one more than the number of folds in the pouch assembly. This allows a substantial surface area to be exposed along each leg of the triple folded filter. In employing a plurality of central openings, frame 62 retains central support members 63a between each opening, and it is across each support member 63a that the folds are made, thus providing strength to the pouch assembly at the folds. Using this technique as just described, it is possible to fold the filter assembly as many times as is practicable in order to increase the surface area for filtration of the parenteral solutions.

To complete the filtration device, whether using a pouch with one or a plurality of folds, filter pouch 50 is enclosed with a flexible, compressible housing formed by two flexible plastic sheets 75 and 76 as shown in FIG. 5. Plastic sheets 75 and 76 are preferably heat sealed to filter assembly pouch 50 along adjacent edges 70 and 72. Concurrently with this heat sealing operation, tubing 41 is sealed between the folded over portions of the pouch along edge 74; edge 74 is also sealed so that tubing 41 provides the only opening or access to the interior of pouch 50. Inlet tubing 44 is concurrently sealed between plastic sheets 75 and 76 to provide the fluid inlet for the filtration device. In plastic sheet 75, which forms one wall of the completed filter housing, there are two small openings 78 provided therethrough, the openings being part of the gas vent feature of the present invention. A preferable construction of the gas vent is illustrated in FIG. 8.

Although plastic sheet 75 includes, in this instance, two small openings 78, the number of openings to allow air or other gases to escape from the housing is not critical and may vary in size and amount depending on many factors including anticipated volume of gas to purge and fabrication requirements. On the surface of plastic sheet 75 which will face the interior of the housing, openings 78 are covered by a membrane filter medium 80 with hydrophobic properties. Hydrophobic filter 80 is preferably disc shaped and is sufficient in size to cover openings 78 in plastic sheet 75. To facilitate the attachment of hydrophobic filter 80 to plastic sheet 75, and to employ heat sealing techniques as the preferable operation of assembly, a support disc 81, porous in nature, is optionally positioned between plastic sheet 75 and hydrophobic filter 80 in the heat sealing step. Support disc 81 is desirably a plastic scrim material which not only provides good heat sealing characteristics but does not affect the flow rate of gas which escapes through hydrophobic filter 80 and passes out of the housing through openings 78. Thus, in the completed filtration device, the gas vent, including hydrophobic filter 81, is attached directly to the interior wall of the housing so that gas or air in the housing may be purged directly out of the housing in the most expedient manner.

The completed structure of this embodiment of the vented filtration device of the present invention is illustrated in FIG. 9. Pouch 50 is shown disposed within passage 48 inside housing 30, with outlet tubing 41 communicating with the interior of pouch 50 through the liquid opening in edge 74. The pouch components and the flexible plastic sheets which form the housing for the filter assembly are sealed along their edges to produce a closed filtration device except for the liquid inlet and outlet formed by tubings 44 and 41 respectively, and gas vent openings 78. In use, liquid from the administration set enters housing 30 of the vented filtration device through inlet tubing 44. As sometimes occurs, gas, such as air, is in the line traveling from the intravenous solution container, and that undesirable air also enters housing 30 of the filtration device with the liquid. FIGS. 10 and 11 graphically illustrate the filtration device of this invention in use and during the passage of liquid therethrough.

Liquid enters the housing through inlet tubing 44 and travels into upstream pressure section 51 of the passage inside housing 30. As liquid enters, pockets or bubbles of air may be mixed with the liquid. Inasmuch as the liquid in upstream pressure section 51 is under positive pressure, the liquid is forced through filter pouch 50, including the hydrophilic filter membrane therein, into downstream pressure section 52 with which outlet tubing 41 communicates. Thus, all liquid passing from inlet 44 to outlet 41 passes through filter assembly pouch 50 thereby filtering out particulate matter, including bacteria, so that the liquid passing out of filter housing 30 has a higher degree of safety before entering the patient.

Inasmuch as the hydrophilic membrane filter in pouch 50 generally has very small openings for filtration purposes, air in the liquid would have a tendency to accumulate on the openings to cause a blockage of liquid flow through the filter pouch. This problem is obviated by inclusion of gas vent 55 in housing 30. By locating gas vent 55 to communicate with upstream pressure section 51, the positive pressure in that section of the passage tends to force air or other gases in the liquid out of openings 78 in plastic sheet 75 of housing 30. The hydrophobic nature of gas vent filter 80 permits air to escape from passage 51, but its non-wetting characteristics prevent any of the liquid from escaping from gas vent 55. Thus, undesirable air in the parenteral liquid entering the filtration device of this invention is purged from the system automatically, thereby eliminating the possibility of air blockage at the liquid filter and assuring unimpeded flow of the liquid through the liquid filter. It is noted in referring to FIGS. 10 and 11 that flexible plastic sheets 75 and 76 defining flexible housing 30 tend to bulge out and separate away from filter pouch 50 within housing 30 so that sufficient volume of liquid may pass through the filtration device.

As oftentimes occurs when employing a filtration device in the administration of intravenous or parenteral liquids, the orientation of the device is unpredictable, with the filtration device lying in any position depending upon where and how it is included in the administration hookup. Accordingly, in using the gas vent feature of the present invention, air must be allowed to escape irrespective of the position of the filtration device during liquid administration. To accomplish this, it has been found preferable to orient filter assembly pouch 50 inside filter housing 30 so that the liquid opening in pouch 50 is connected to outlet tubing 41, rather than to inlet tubing 44. The effect of this construction, plus the fact that positive liquid pressure is in upstream pressure section 51 inside housing 30, would normally cause flexible filter pouch 50 to collapse on itself thereby impeding or possibly completely blocking liquid flow through the filtration device. To overcome the collapse of filter pouch 50, the scrim materials 66 are disposed within filter pouch 50.

In FIG. 11, it can be seen that scrim material 66 prevents the walls of pouch 50 from completely collapsing on themselves to prevent liquid from flowing through the filtration device. The force of the liquid from upstream pressure section 51 forces each wall of filter pouch 50 inwardly toward each other. However, the liquid force urges each surface of the folded scrim toward each other so that the points of ridges 67 on each folded portion prevent complete surface to surface contact of the maintenance member (these points are exaggerated in FIG. 11 to better define this function). Accordingly, channels 69 are maintained between ridges 67. Liquid passing through filter pouch 50 passes through the pores of scrim material 66 to channels 69 which carry the flowing liquid through filter pouch 50 in downstream pressure section 52 to outlet tubing 41. Thus, liquid flow is assured through the filtration device having a construction wherein air is automatically purged therefrom irrespective of its position during liquid administration. Other configurations of scrim material are readily conceivable to provide a channel inside filter pouch 50 to carry the flowing liquid to outlet tubing 41, the scrim material illustrated in the drawings herein merely being a preferable embodiment.

The preferred embodiment of the present invention contemplates the use of a unique hydrophilic membrane filter material which has certain properties that are superior to the properties of other filter media usable with the invention. This unique hydrophilic membrane filter material is a non-woven nylon substrate coated with (or sometimes impregnated with) a copolymer of acrylonitrile and polyvinylchloride. The preferred thickness of the membrane is about 0.007 inch (0.018 cm.), while the pore size is about 0.2 microns.

Other membrane filter media are usable with the present invention, such as membranes formed from mixed esters of cellulose reinforced with a polyester mesh.

While various filter membranes may be used as the hydrophobic filter, it has been found preferable to use porous polytetrafluoroethylene film as this filter material. In most applications, the pore size of this hydrophobic filter is about 0.2 microns, while the thickness of the membrane is about 50 microns. Generally, the size of the hydrophobic filter is much smaller than the hydrophilic filter since the volume of air to be purged is not great; however, size of the hydrophobic filter is not critical, and can be selected generally according to choice, practicability and fabrication convenience.

Although all of the materials utilized in the construction of the filtration device of the present invention are not critical, it will be appreciated that the materials should preferably be bio-compatible and that, in order to facilitate fabrication of the filtration device, most of the materials should desirably be heat-sealable. By way of example, the outer plastic sheets of the flexible housing are preferably formed from polyvinylchloride having a thickness of 8 mils (0.02 cm.). Likewise, all of the tubing, including tubing 32, 41 and 44, are preferably constructed of polyvinylchloride. The size of the filter assembly pouch and the housing are generally left to the option of the designer to fulfill the intended purposes and uses of the present invention; however, it has been found that the overall dimensions should be limited, optimized or relatively proportioned in order to conveniently position the filter assembly on the arm of a patient but at the same time provide the superior flow rates and operating pressures achievable with this unique filter structure. The presently preferred outside dimensions for the filter housing are 3 inches (7.62 cm.) from the distal to the proximal end, and 13/16 inches (2.07 cm.) wide, in the lay-flat condition.

Thus, it is apparent that there has been provided in accordance with the invention a vented flexible filtration device that fully satisfies the aims, advantages and aspects as set forth above.

I claim:

1. A vented filtration device for use in the filtration of parenteral liquids comprising: a closed, flexible and compressible housing having a liquid inlet and a liquid outlet, said housing including an internal passage connecting said inlet and outlet; a filter assembly disposed within said passage between said inlet and said outlet thereby defining an upstream pressure section between said inlet and said assembly and a downstream pressure section between said assembly and said outlet, said filter assembly including a flexible porous, bacteria retentive filter membrane having a pore size not greater than 0.22 microns, a flexible, porous support material having pores generally greater in size than those of said filter membrane overlying one surface of said filter membrane, and a flexible frame overlying the surface of said filter membrane opposite said supported surface, said frame having at least one central opening exposing a substantial surface area of said filter membrane, said filter assembly adapted to filter all liquid passing from said inlet to said outlet during use; said filter assembly including at least one fold to form said filter membrane into a pouch having an open end facing toward said downstream pressure section and having a closed end facing said upstream pressure section; and gas vent means through said housing communicating with said upstream pressure section of said passage adapted to allow gas but not liquid to pass from said upstream section out of said housing whereby gas entering said upstream section will not clog said filter membrane, said filter assembly providing a sufficiently low pressure drop thereacross, so as to eliminate the requirement of a pump to force said fluid through said assembly and said assembly capable of being deformed and still maintain fluid flow without the requirement of a pump to force said fluid through said assembly.

2. The device of claim 1 wherein said outlet communicates with the interior of said filter assembly pouch through said liquid opening.

3. The device of claim 1 wherein said housing is comprised of a pair of flexible sheets sealed together around their peripheries and said pouch has seal means along two edges adjacent said folded edge, said seal for said housing and for said pouch along the respective edges being a common seal.

4. The device of claim 1 herein said filter membrane is a porous non-woven nylon substrate coated with a copolymer of acrylonitrile and polyvinylchloride having a general pore size of about 0.2 microns.

5. The device of claim 1 wherein said gas vent means includes an opening through said housing and a hydrophobic filter medium attached to said housing to cover said opening, thereby allowing only gas to escape therethrough.

6. The device of claim 5 wherein said hydrophobic medium is a porous film of tetrafluoroethylene film having a general pore size of about 0.2 microns.

7. The device of claim 1 wherein said filter assembly includes means for preventing the collapse of said pouch on itself during liquid flow from said upstream section through said filter assembly to said downstream section.

8. The device of claim 7 wherein said collapse preventing means is a porous scrim fabric positioned as the innermost layer of said folded pouch so that each folded surface opposes each other.

9. The device of claim 7 wherein said filter assembly pouch has at least three folds to increase the filtration surface area of said device and wherein said filter assembly includes a porous scrim fabric on the innermost and outermost layers of said assembly so that, when said assembly is folded three times in the pouch formation, collapse on itself is prevented during use.

10. A vented filtration device for use in the filtration of parenteral liquids comprising: a closed, flexible and compressible housing including a pair of flexible sheets sealed together around their peripheries except for a liquid inlet and a liquid outlet, said housing including a passage within connecting said inlet and outlet; a filter assembly disposed within said passage between said inlet and said outlet thereby defining an upstream pressure section between said inlet and said assembly and a downstream pressure section between said assembly and said outlet, said filter assembly including a flexible, porous bacteria retentive filter membrane having a pore size not greater than 0.22 microns, a flexible, porous support material having pores generally greater in size than those of said filter membrane overlying one surface of said filter membrane, a flexible frame overlying the surface of said filter membrane opposite said supported surface, said assembly being folded at least three times and sealed to form a flexible pouch having one liquid opening in one ene thereof, said outlet communicating with the interior of said pouch through said liquid opening, said frame having one more central opening than the number of folds to expose a substantial surface area along each leg of said folded filter, said assembly including a porous scrim fabric on the innermost and outermost layers thereof so that collapse of said folded pouch on itself is prevented during use, said filter assembly adapted to filter all liquid passing from said inlet to said outlet during use; and a gas vent opening through one of said flexible housing sheets communicating with said upstream pressure section of said passage and a hydrophobic filter medium attached to said housing sheet to cover said opening to thereby allow gas not liquid to pass from said upstream section out of said housing, said filter assembly providing a sufficiently low pressure drop thereacross, so as to eliminate the requirement of a pump to force said fluid through said assembly.

* * * * *